United States Patent
Frey et al.

(10) Patent No.: US 10,874,288 B2
(45) Date of Patent: Dec. 29, 2020

(54) SHANK INSTRUMENT

(71) Applicant: Richard Wolf GmbH, Knittlingen (DE)

(72) Inventors: Sebastian Frey, Waghäusel (DE); Eberhard Körner, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 565 days.

(21) Appl. No.: 15/355,676

(22) Filed: Nov. 18, 2016

(65) Prior Publication Data
US 2017/0143189 A1    May 25, 2017

(30) Foreign Application Priority Data
Nov. 19, 2015    (DE) .......................... 10 2015 222 858

(51) Int. Cl.
*A61B 1/005* (2006.01)
*A61B 17/32* (2006.01)
(Continued)

(52) U.S. Cl.
CPC ........ *A61B 1/0051* (2013.01); *A61B 1/00135* (2013.01); *A61B 17/32* (2013.01);
(Continued)

(58) Field of Classification Search
CPC ............ A61B 1/0051; A61B 2017/003; A61B 2017/00305; A61B 2017/00309; A61B 2017/00314; A61B 2017/00318; A61B 2017/00323; A61B 2017/00327; A61B 2017/00331; A61M 2025/015; A61M 2025/0161; A61M 2025/0163; A61M 25/0105; A61M 25/0133; A61M 25/0138;
(Continued)

(56) References Cited

U.S. PATENT DOCUMENTS 5,807,241 A * 9/1998 Heimberger ......... A61B 1/0055
600/139
5,851,212 A    12/1998 Zirps et al.
(Continued)

FOREIGN PATENT DOCUMENTS

DE    10 2006 000 399 A1    2/2008
DE    20 2009 007 979 U1    8/2009

*Primary Examiner* — Tan-Uyen T Ho
*Assistant Examiner* — Chima U Igboko
(74) *Attorney, Agent, or Firm* — McGlew and Tuttle, P.C.

(57) ABSTRACT

A shank instrument, particularly a medical-endoscopic shank instrument includes a hollow shank which between two rigid parts includes a part which is bendable transversely to a hollow shank longitudinal extension. The bendable part is fixedly connected to at least one of the rigid parts, in a manner such that two projections which are formed on a peripheral wall of one of the parts connected to one another, are arranged lying opposite one another on a peripheral wall and project in a direction of a longitudinal axis of the part, positively engage into two recesses which are formed lying opposite one another on a peripheral wall of the other part and which completely break through the peripheral wall. At the outer periphery, the parts of the hollow shank which are positively connected to one another, in the region of the positive connection are surrounded by a component.

16 Claims, 9 Drawing Sheets

(51) Int. Cl.
  *A61B 1/00* (2006.01)
  *A61B 90/00* (2016.01)
  *A61B 17/29* (2006.01)
(52) U.S. Cl.
  CPC .............. *A61B 17/320016* (2013.01); *A61B 2017/2901* (2013.01); *A61B 2017/2908* (2013.01); *A61B 2090/0813* (2016.02)
(58) Field of Classification Search
  CPC .......... A61M 25/0141; A61M 25/0144; A61M 25/0147; A61M 25/0158
  USPC ........................................ 600/127, 128, 129
  See application file for complete search history.

(56) References Cited

U.S. PATENT DOCUMENTS

| | | |
|---|---|---|
| 6,645,218 B1 | 11/2003 | Cassidy et al. |
| 8,419,720 B1 | 4/2013 | Dawoodjee |
| 2009/0299343 A1* | 12/2009 | Rogers ............... A61B 1/00078 606/1 |
| 2012/0083770 A1 | 4/2012 | Paik et al. |
| 2014/0025045 A1* | 1/2014 | Abt .................. B29C 65/48 606/1 |

* cited by examiner

SHANK INSTRUMENT

CROSS REFERENCE TO RELATED APPLICATIONS

This application claims the benefit of priority under 35 U.S.C. § 119 of German Application 10 2015 222 858.4 filed Nov. 19, 2015, the entire contents of which are incorporated herein by reference.

FIELD OF THE INVENTION

The invention relates to a shank instrument, in particular to a medical-endoscopic instrument shank instrument.

BACKGROUND OF THE INVENTION

Instruments of the type being discussed here are applied as standard in the field of minimal-invasive surgery. There, its shank is introduced through a natural or artificially created access channel, into the inside of the body of the patient to be treated, so that a tool which is arranged at the distal end of the shank can be arranged in the direct proximity of the object being treated, whereas devices for the control of the tool and which are arranged at the proximal side of the shank are located outside the patient in a manner in which they are easily accessible to the operator.

Apart from such shank instruments, with which the tool is arranged in the direct longitudinal extension of a rigid, straight shank, an instrument is known from U.S. Pat. No. 5,851,212 A, with which a distal end section of the shank is bendable transversely to the longitudinal axis of the shank. Whereas the first-mentioned shank instruments reach the limits of their effectiveness particularly if only a very narrow access channel is available to the instrument, and operative manipulations need to be carried out with the tool arranged at the distal end of the shank, laterally of an access axis defined by the access channel, the instrument known from U.S. Pat. No. 5,851,212 A appears to be better suited in the case of such conditions, due to the bendability of its distal end section.

With regard to this instrument, it is the case of a so-called shaver for removing body tissue. For this purpose, this instrument comprises a rotating cutting tool with a cutter which is aligned parallel to the rotation axis of this tool and which is arranged in an instrument head, said instrument head being arranged distally of the bendable shank section and forming a counter-cutter to the cutter of the cutting tool.

A significant constituent of the bendable shank section of this instrument is a helical spring which is bendable transversely to its longitudinal axis, with one end is welded to the rigidly designed proximal shank section and with the other end is welded to the instrument head. A metal strip which is welded to the helical spring as well as to the proximal shank section and to the instrument head is arranged on the radial outer side of the helical spring. The helical spring and the metal strip are moreover surrounded by a plastic sheath which is shrunk onto the helical spring. Inasmuch as this is concerned, it is particularly the manufacture of the bendable section of the instrument known from U.S. Pat. No. 5,851, 212 A which is comparatively time-consuming and costly.

SUMMARY OF THE INVENTION

Against this background, it is an object of the invention, to create a shank instrument of the previously described type, with a shank section which is laterally deflectable relative to a proximal shank section, said instrument demanding less manufacturing effort whilst maintaining a high reliability.

According to the invention, a shank instrument, in particular a medical-endoscopic shank instrument, is provided comprising an outer peripheral component and a hollow shank. The hollow shank comprises two rigidly configured parts and a bendable part which is bendable transversely to a longitudinal extension of the hollow shank, between the two rigidly configured parts, and which is fixedly connected to at least one of the two rigidly configured parts such that two projections formed on a peripheral wall of one of the rigidly configured parts connected to one another, are arranged lying opposite one another on the peripheral wall and project in a direction of a longitudinal axis of the rigidly configured part, positively engage into two recesses which are formed lying opposite one another on the peripheral wall of the bendable part and which completely pass through the peripheral wall form a positive connection. The parts of the hollow shank which are positively connected to one another, in a region of the positive connection, are surrounded by the outer peripheral component at an outer periphery thereof.

The shank instrument according to the invention is preferably a medical-endoscopic shank instrument, but with regard to this, it can also be the case of a technoscope which is applied in the technical field. The shank instrument is equipped with a hollow shank which between two rigidly designed parts comprises a part which is bendable transversely to its longitudinal extension. The hollow shank is therefore provided with a rigid, proximal part which is preferably aligned in a straight manner and onto which a part connects, said part being able to be bent from a position in which it is aligned in the direct longitudinal extension of the proximal part of the hollow shank, into a direction transverse to a longitudinal axis of the proximal part of the hollow shank. A second, rigidly designed part of the hollow shank which preferably forms a distal instrument head of the shank instrument, in which head a tool of the shank instrument is mounted, is subsequent to the bendable part at the distal side.

According to the invention, the bendable part of the hollow shank is fixedly connected to at least one of the other parts of the hollow shank via a positive-fit connection. The positive connection of the bendable part to one or preferably to both of the other parts of the hollow shank, in contrast to the material connection of the bendable part of the hollow shank to the rigidly designed proximal part of the hollow shank and to the instrument head, and known from the state of the art, has the advantage that the three parts of the hollow shank, which is to say its two rigidly designed parts and the bendable part arranged therebetween, can consist of the most different of materials, so that the bendable part of the hollow shank for example can be inexpensively manufactured of plastic which makes sense with regard to its bendability, whilst with regard to the two other parts of the hollow shank it can be the case of metal parts.

According to the invention, one envisages two projections which are formed on a peripheral wall of one of the parts connected to one another, are arranged on the peripheral wall in a manner lying opposite one another and project in the direction of the longitudinal axis of the part, positively engaging into two recesses which are formed lying opposite one another on the peripheral wall of the other part and which completely break through the peripheral wall. Accordingly, two projections project on the peripheral wall of the first part of the hollow shank, in the axial direction of the part and typically in the direction of the second part which is to be connected thereto, wherein these two projections lie opposite one another and preferably diametrically opposite one another, which is to say lie opposite one another on a connection line intersecting the middle axis of this part. In a manner corresponding to this, two recesses which are complementary to the projections of the first part, completely break through the peripheral wall of this first part and likewise lie opposite one another or preferably diametrically opposite one another on a connection line intersecting the middle axis of this part, are formed on the second part of the hollow shank which is connected to the first part, on the outer periphery of this second part, at an end facing the first part, wherein the projections of the first part and the recesses of the second part typically comprise undercuts which effect a positive fit between the first and the second part to be connected thereto, in the direction of the longitudinal extension of the hollow shank. The arrangement of the projections on the first part of the hollow shank in combination with the arrangement and the design of the second part of the hollow shank advantageously permits a rapid and simple assembly of the first part on the second part, since for this, the first part, departing from a position, in which its projections are arranged in a direct, straight line to the recesses of the second part at the outside of the second part, merely needs to be moved in a straight direction relative to the second part, until each of its projections is engaged in a recess of the second part.

According to the invention, a component which surrounds the parts which are thus positively connected to one another is provided, due to the fact that the two parts of the hollow shank which are connected in the described manner are only fixed in the axial direction of the hollow shank due to the engagement of the projections of the first part into the recesses of the second part. The two parts of the hollow shank are prevented from moving relative to one another in the radial direction by way of this, so that they are also positively connected to one another in the radial direction of the hollow shank. A particularly simple assembly of this component surrounding the two parts to be connected to one another is possible if the component is designed in an annular manner and has an inner cross section which corresponds to the outer cross section of the parts of the hollow shank which are to be connected to one another, so that the component merely needs to be stuck onto the hollow shank, until the component is located directly outside the positive connection between the one and the other part of the hollow shank. The component is usefully dimensioned such that it only covers the bendable part of the hollow shank to a limited extent, in order in this manner not to prevent or obstruct its bending.

According to an advantageous further development of the shank instrument according to the invention, the distal part of the hollow shank is positively connected to the bendable part of the hollow shank in the previously described manner. In this case, a sleeve which is connected to the distal end of the hollow shank and which radially surrounds the positive connection between the distal part and the bendable part is preferably provided. Hereby, the projections are preferably arranged on the distal part of the hollow shank, whereas the recess into which the projections engage, are formed on the bendable part of the hollow shank, for the positive fixation of the distal part in the direction of the longitudinal axis of the hollow shank. In this case, the connection between the sleeve and the distal part of the hollow shank can advantageously be realized by way of the projections formed on the distal part not only projecting in the axial direction of this but also in the radial direction of this, and engaging in openings which are formed on the sleeve and correspond to the projections. The sleeve becomes immovable with respect to the distal part of the hollow shank and with respect to its bendable part, on account of this. The distal part and the sleeve can also be materially connected to one another, for example by way of a laser welding, additionally or alternatively to this fixation of the sleeve.

According to a further, preferred design of the shank instrument according to the invention, the bendable part of the hollow shank is positively connected to the proximal part of the hollow shank in the previously described manner. Hereby, an outer tube radially surrounds the positive connection between the bendable and the proximal part of the hollow shank, wherein the hollow shank is axially movable relative to the outer tube. The outer tube usefully extends up to a handle which is arranged proximally on the instrument shank, wherein the hollow shank in the handle projects out of the outer tube at the proximal side and in this region is actively connected to a control device, with which it is axially moveable relative to the outer tube. With regard to this movability of the hollow shank, the significance of which will be dealt with in yet more detail hereinafter, it is evidently to be understood that the movement path of the hollow shank relative to the outer tube is limited in a manner such that the outer tube always surrounds the positive connection between the bendable and the proximal part of the hollow shank.

A pull element which is fastened on the hollow shank, at the distal side of the bendable part or on the hollow shank in the region of the end of the bendable part and effects a lateral deflection of the bendable part given a force application, is usefully provided for bending the bendable part of the hollow shank. According to the invention, a design with which the sleeve connected to the distal part of the hollow shank is connected to such a pull element for the control of the bending of the bendable part of the hollow shank is preferred.

In particular, in a further development of this design, it is particularly advantageous if, as is further preferably envisaged, the pull element is connected to the outer tube which radially surrounds the positive connection between the bendable and the proximal part of the hollow shank. In this case, the pull element is therefore not only connected to the sleeve forming part of the positive connection between the distal and the bendable part of the hollow shank, but also to the outer tube. If with this design, a movement force acting in the distal direction of the hollow shank is exerted onto this hollow shank, then a movement of the hollow shank entailed by this is only possible amid simultaneous bending of the bendable part of the hollow shank, and the bendable part is therefore laterally deflected in dependence on the movement path of the hollow shank.

It is above all with regard to an as small as possible number of components of the shank instrument that one preferably envisages the sleeve and the pull element being formed by a common component. A thin-walled tube, whose wall is removed in an angular region for example of 340 or more, with the exception of an end section forming the sleeve, so that a narrow material strip which projects in the axial direction and which forms the pull element remains on the end section forming the sleeve, is usefully applied for creating this component.

The bendable part of the hollow shank is preferably formed by a tube. The bendable part is advantageously formed from an elastic material, in order to permit a lateral deflection of this, wherein it comprises several incisions running transversely to its longitudinal extension and distributed over its length. Hereby, several of the incisions are usefully formed on the outer side of the bendable part of the hollow shank, at the outer side of which incisions the pull element is arranged for the control of the lateral deflection of the bendable part, and in the direction of said element the bendable part is deflectable. The incisions are favorably designed widened in a wedge-like manner, so that a bending of this part of the hollow shank does not entail a displacement of material into the inner lumen of this part of the hollow shank.

For this purpose, one also advantageously envisages directly consecutive incisions being formed on wall regions of the bendable part of the hollow shank, said wall regions lying directly opposite one another. Accordingly, an incision formed on a wall region facing the pull element arranged at the outside of the bendable part of the hollow shank, is followed by an incision formed on a wall region which is away from the pull element, and this incision is again followed an incision formed on the wall region facing the pull element. Typically, further incisions which are arranged on the bendable part of the hollow shank in the described manner can follow this last-mentioned incision.

It is of great importance that the pull element is always aligned parallel to the bendable part of the hollow shank, for a defined lateral deflection of the bendable part of the hollow shank. Above all, a further advantageous development of the instrument according to the invention caters to this, according to which several prominences through which the pull element is led are formed on the bendable part of the hollow shank at the outer side. The pull element always bears tightly on the bendable part, independently of a curvature of this part, as a result of the leading of the pull element through the prominences which are formed on the bendable part of the hollow shank and in which the pull element is freely movable in its axial direction.

Generally, the type of a tool used in combination with the shank instrument according to the invention and, entailed by this, the application purpose of the shank instrument according to the invention is arbitrary to a large extent. Due to the bendable part of its hollow shank and the lateral deflectability of a tool arranged distally of the bendable part, which this entails, this shank instrument however is particularly suitable for the removal of body tissue and in particular with the tissue removal concerning invertebral disc operations, with which the tool can be aligned particularly precisely to the tissue to be removed, so that the danger of damage to other tissue is significantly reduced. Inasmuch as this is concerned, with regard to the instrument according to the invention, it is preferably the case of a cutting instrument, with which a cutting tool which is at least partly exposed in the distal part of the hollow shank is arranged there, wherein this cutting tool is driven in rotation by a drive shaft led through the hollow shank.

The invention is hereinafter explained in more detail by way of one embodiment example represented in the drawings.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

Represented in the drawings in a schematically simplified manner and in different scales.

DESCRIPTION OF THE PREFERRED EMBODIMENTS

With regard to the shank instrument represented in the drawing, it is the case of a cutting instrument for removing body tissue. This shank instrument comprises an elongate hollow shank 2 which is designed in a three-part manner and comprises a proximal part 4 which is directed in a straight manner, a bendable part 6 connecting distally thereto and a part 8 forming the distal end of the shank instrument. A handle is arranged at the proximal side of the hollow shank 2, of which handle only an insert 10 is shown in the drawing for reasons of a better overview, wherein this insert engages into a housing of the handle and contains a control device 40 for the control of a lateral deflection of the bendable part 6.

The part 8 forms an instrument head of the shank instrument, in which a cutting tool 12 is rotatably mounted, said tool being actively connected via a drive shaft 46 led through the hollow shank 2 (see FIG. 9), to a drive motor which is arranged in the handle arranged at the proximal side of the hollow shank 2 and which is likewise not represented. The cutting tool 12 has an essentially cylindrical main body, on whose peripheral side a window is formed, wherein two longitudinal sides of the window which run in the axial direction of the cutting tool 12 form two cutters 14 and 16. The cutters 14 and 16 are exposed at a window 18 which is formed on the part 8 forming the instrument head (see in particular FIG. 2).

Figure 1:
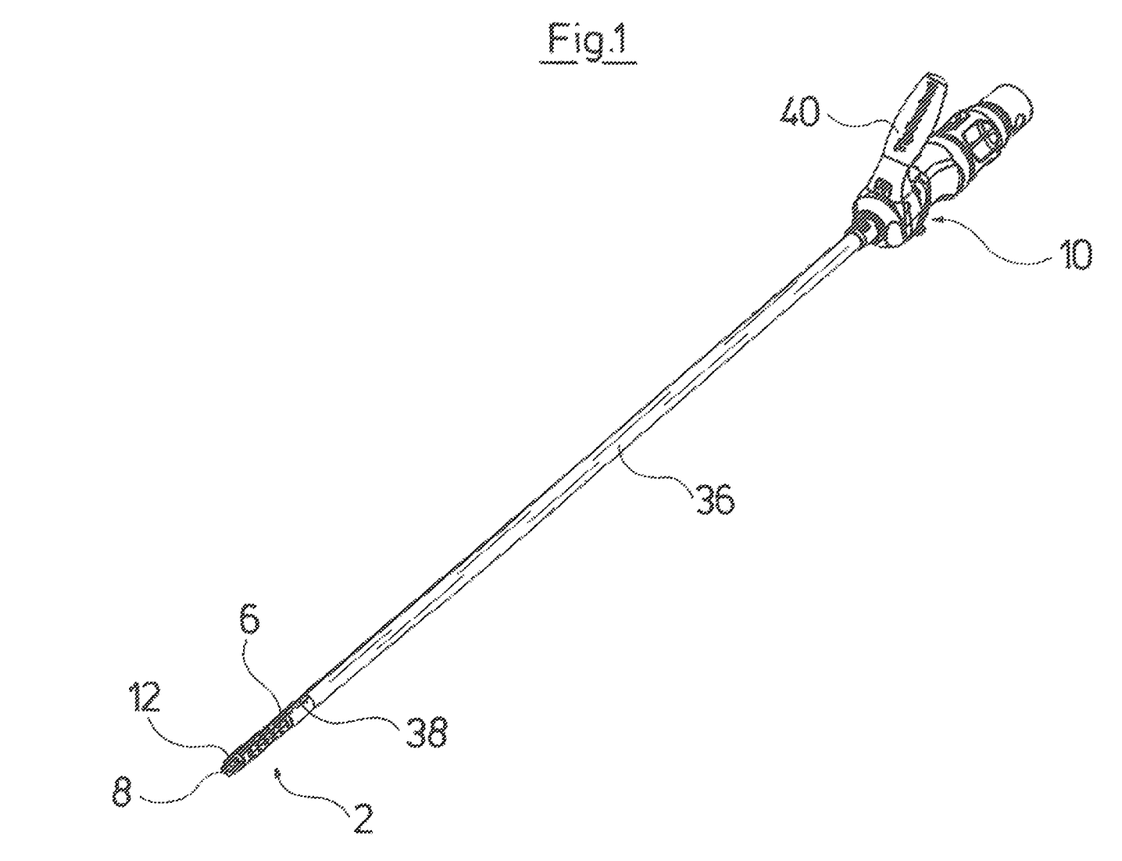
FIG. 1 is a perspective representation of a medical-endoscopic shank instrument.
Figure 2:
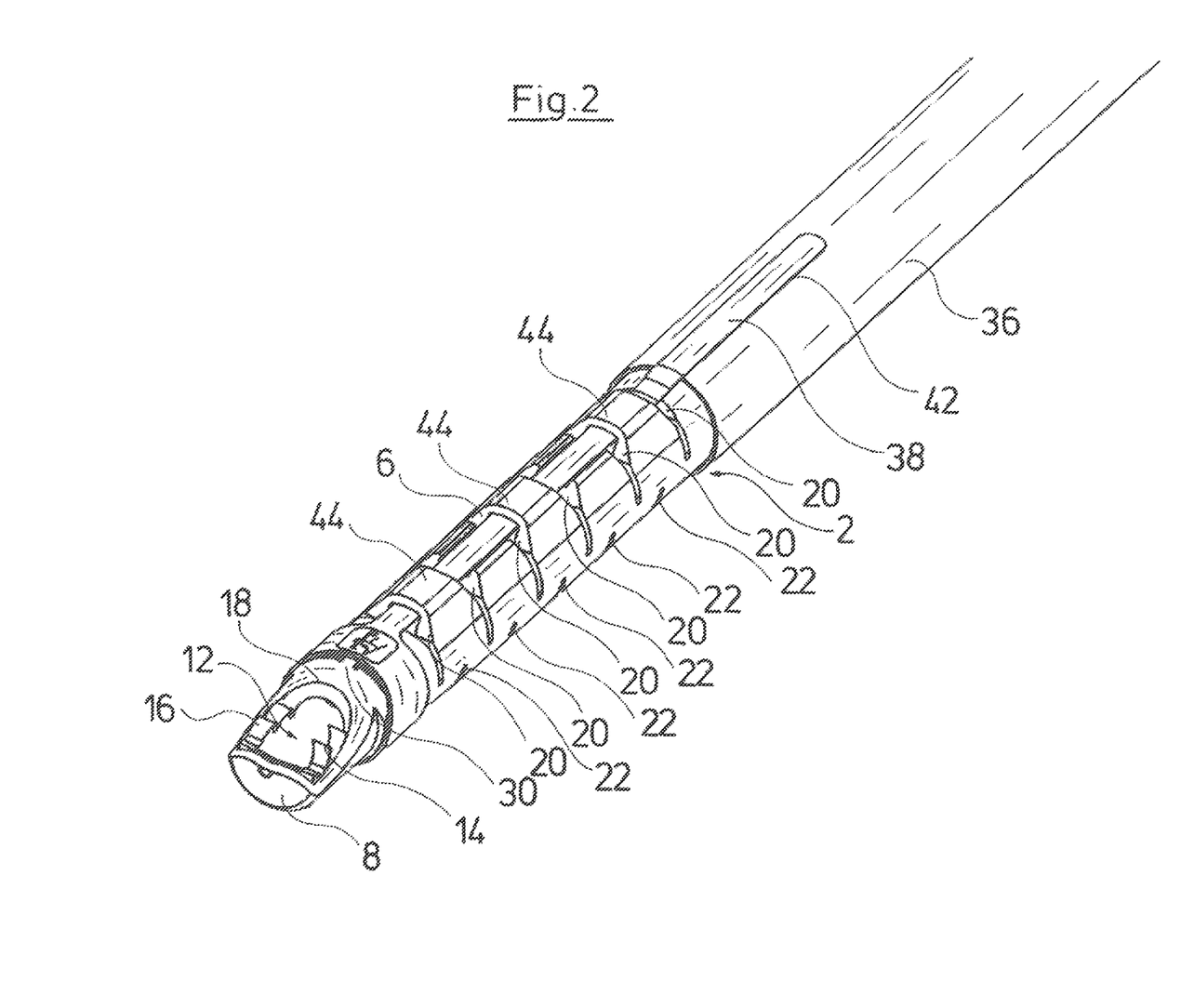
FIG. 2 is a perspective representation of a distal end region of the shank instrument according to FIG. 1.
Figure 3:
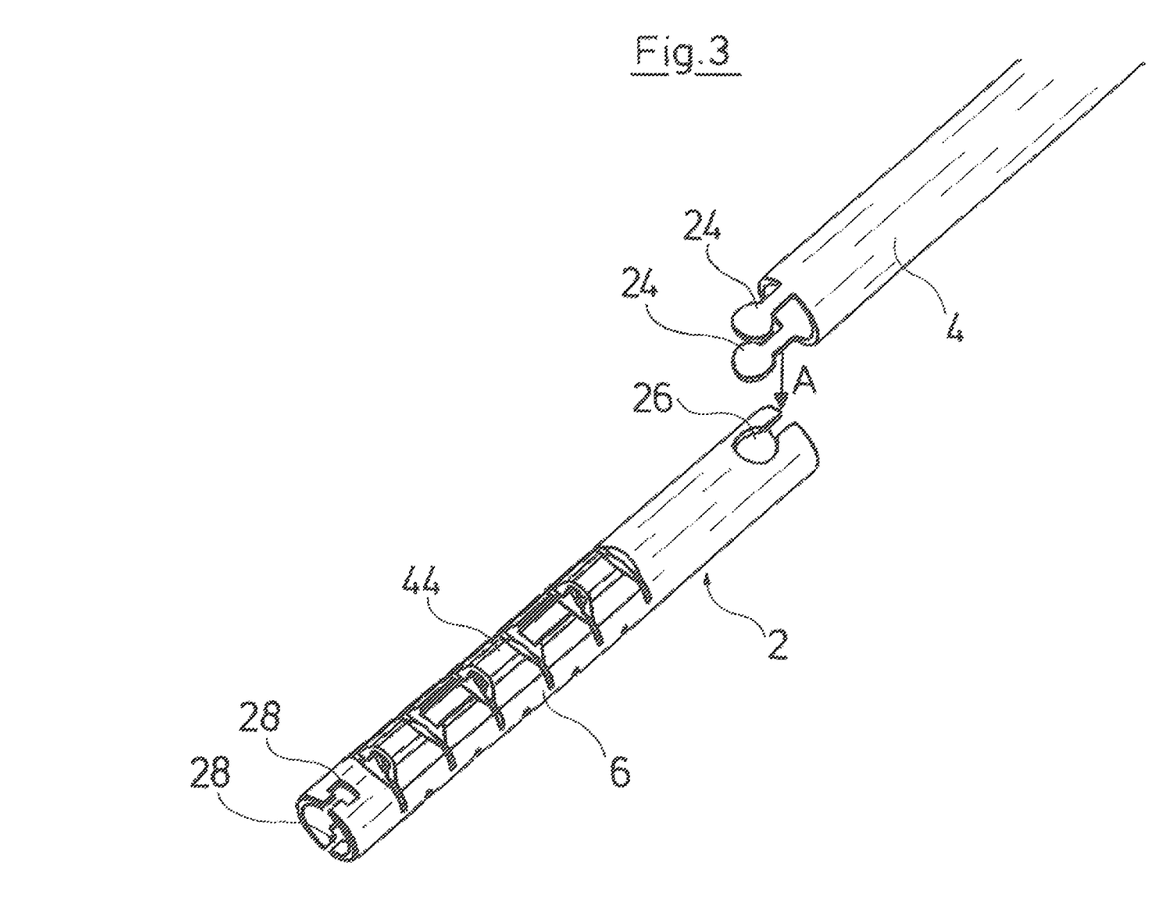
FIG. 3 is a perspective exploded representation of a proximal part of a shank of the instrument shank according to FIG. 1, and a bendable part of this which connects thereto.
Figure 4:
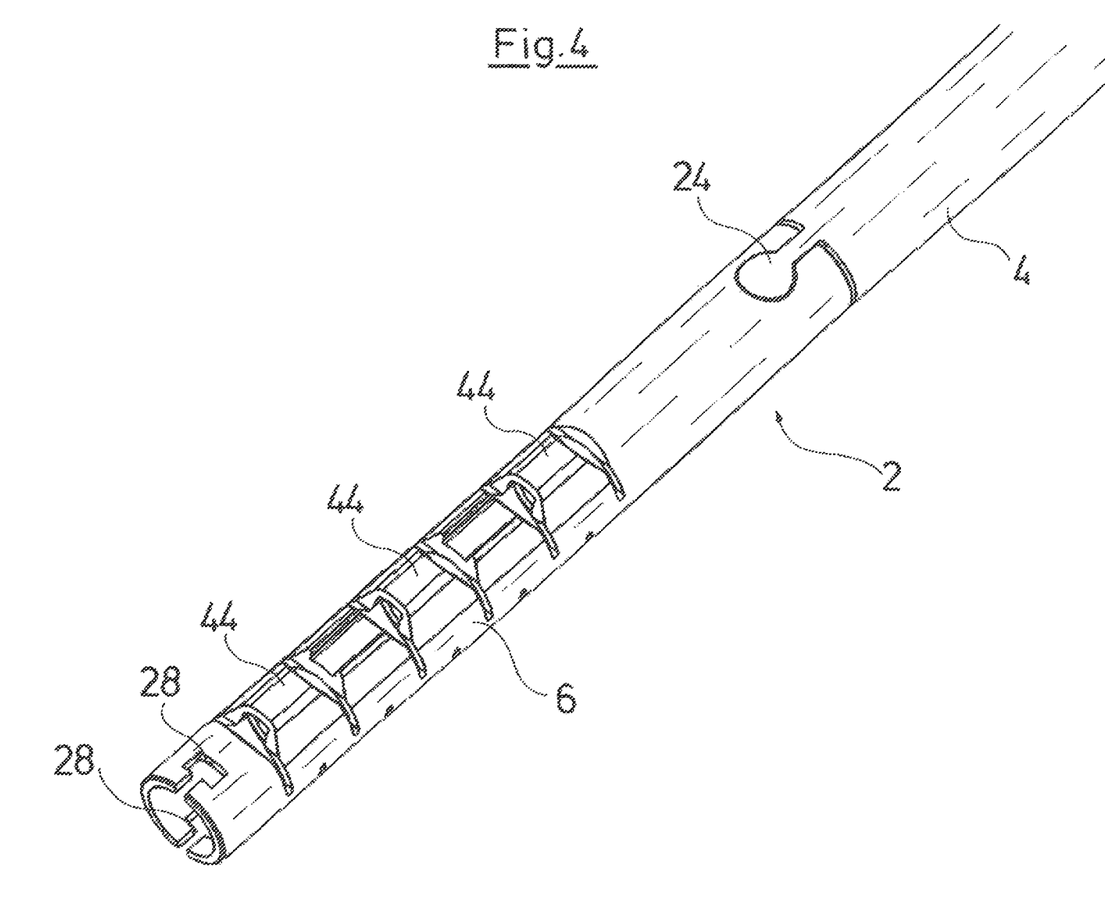
FIG. 4 is a representation according to FIG. 3, in the joined-together condition.
Figure 5:
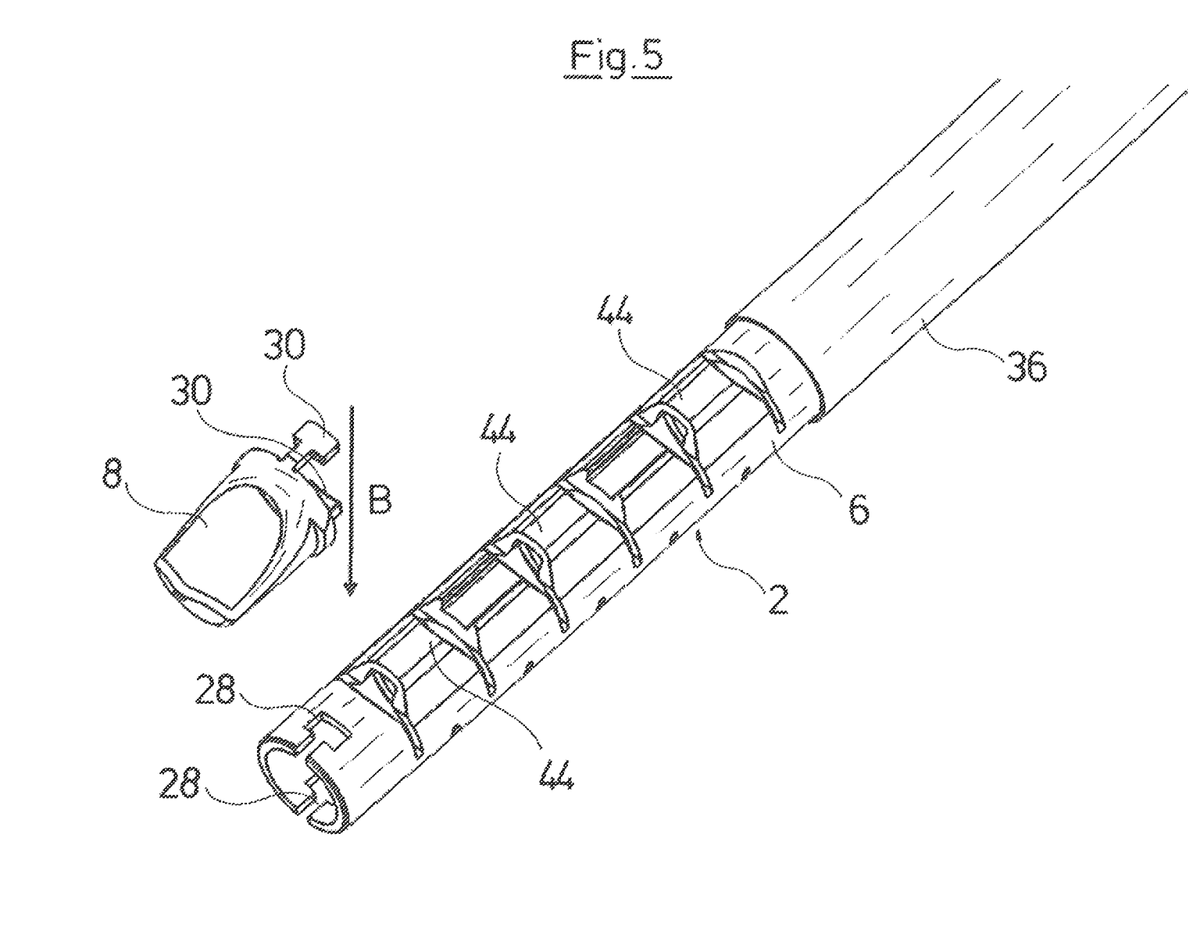
FIG. 5 is a perspective exploded representation of the bendable part of the shank and a distal part of the shank which connects to this, of the shank instrument according to FIG. 1.
Figure 6:
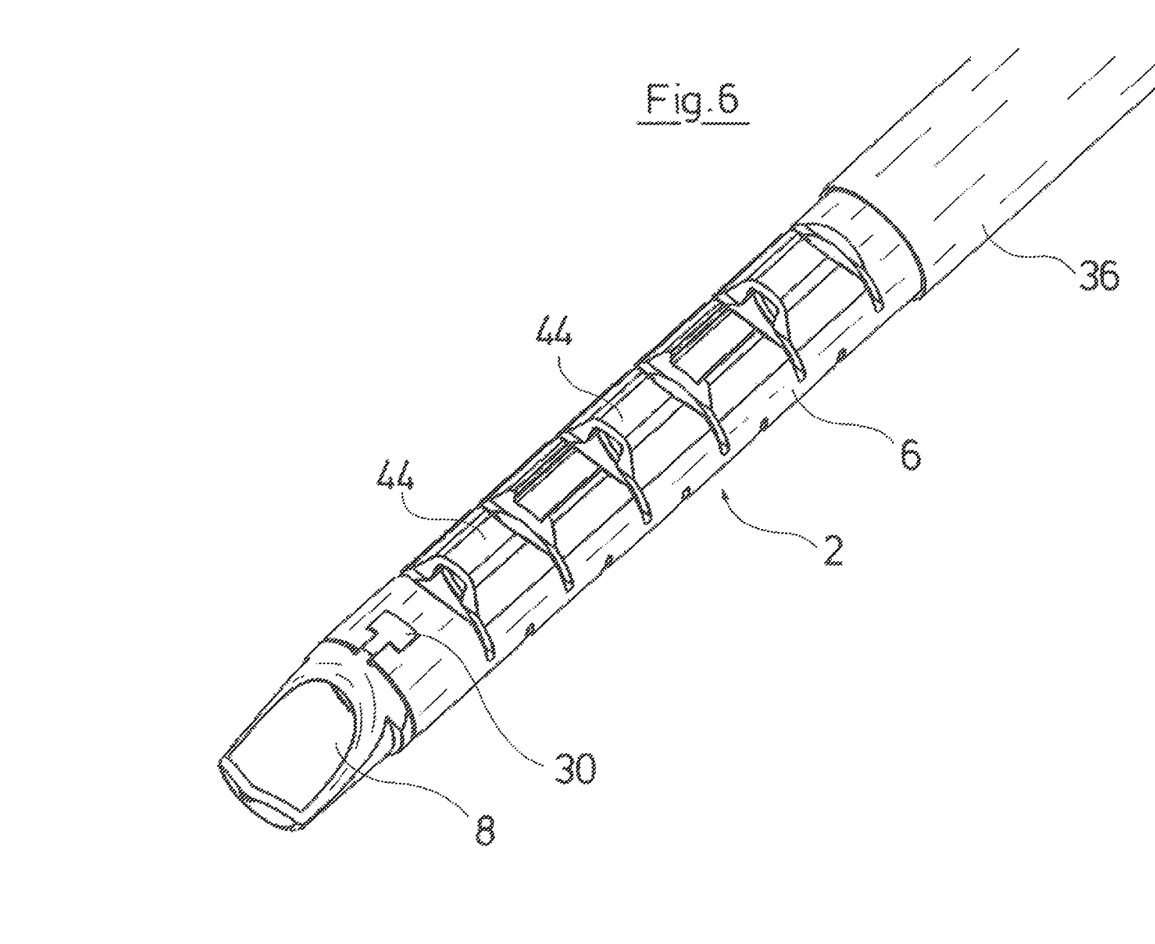
FIG. 6 is a representation according to FIG. 5, in the assembled condition.

The bendable part 6 of the hollow shank 2 is laterally deflectable transversely to the longitudinal extension of the proximal part 4 of the hollow shank 2 which is designed in a rigid manner as is the case with the part 8 of the hollow shank 2. For this purpose, the essentially tubularly designed part 6 of the hollow shank 2 is formed from an elastic plastic and comprises several incisions 20 and 22 distributed over its length. Each of these incisions 20 and 22 is aligned transversely to the longitudinal extension of the part 6 and is widened outwards in a wedge-like manner. Hereby, the incisions 20 are arranged on a common wall region of the part 6, in a manner distanced to one another in the longitudinal direction of the part 6, whereas the incisions 22 which are formed between the incisions 20 in the longitudinal direction of the part 6 are formed on a wall region of the part 6 which lies directly opposite the first-mentioned wall region (FIG. 2).

It is evident from FIGS. 3-6 that the part 6 of the hollow shank 2 which lies between the parts 4 and 8 is positively connected to the parts 4 and 8.

Two essentially T-shaped projections 24 are formed on the peripheral wall of the part 4, at the distal end of the proximal part 4 of the hollow shank 2, for the connection of the bendable part 6 to the proximal part 8 of the hollow shank 2. These two projections 24 are arranged lying diametrically opposite one another, on the peripheral wall of the part 4, and point in the distal direction. Two T-shaped recesses 26 which completely break through the peripheral wall of the part 6 and which likewise lie diametrically opposite one another are formed on the bendable part 6 of the hollow shank 2, in a manner departing from the proximal end of this shank, and in a manner corresponding to the projections 24 formed on the part 4 of the hollow shank 2. As is evident from FIG. 3, for joining the parts 4 and 6 of the hollow shank 2, the part 4 is positioned with respect to the part 6, such that its projections 24 are arranged in a straight line at the outer side of the recesses 26 formed on the bendable part 6, wherein the projections 24 of the part 4 can be brought to engage into the recesses 26 of the part 6 of the hollow shank in a simple manner by way of a movement of the part 4 in a direction A, by which means the part 6 is positively fixed on the part 4 of the hollow shank 2 in the longitudinal direction of the hollow shank 2.

Two further T-shape recesses 28 which lie diametrically opposite one another in a plane normal to the arrangement of the recesses 26 are formed on the peripheral wall of the part 6, in a manner departing from the distal end of the part 6 of the hollow shank 2. Two T-shaped projections 30 which project on the part 8 in the proximal direction and are arranged lying diametrically opposite one another on the peripheral wall of the part 8 are formed on the peripheral wall of the distal part 8 of the hollow shank 2, in a manner corresponding to these recesses 28. It can be recognized from FIG. 5 that the part 8 is positioned with respect to the part 6 such that its projections 30 are arranged in a straight line at the outer side of the recesses 30 formed on the bendable part 6, for joining together the parts 6 and 8 of the hollow shank 2, wherein the projections 30 of the part 8 can be brought to engage with the recesses 28 of the part 6 of the hollow shank 2 by way of a movement of the part 8 in a direction B, by which means the part 8 is positively fixed on the part 6 of the hollow shank 2, in the longitudinal direction of the hollow shank 2.

Figure 7:
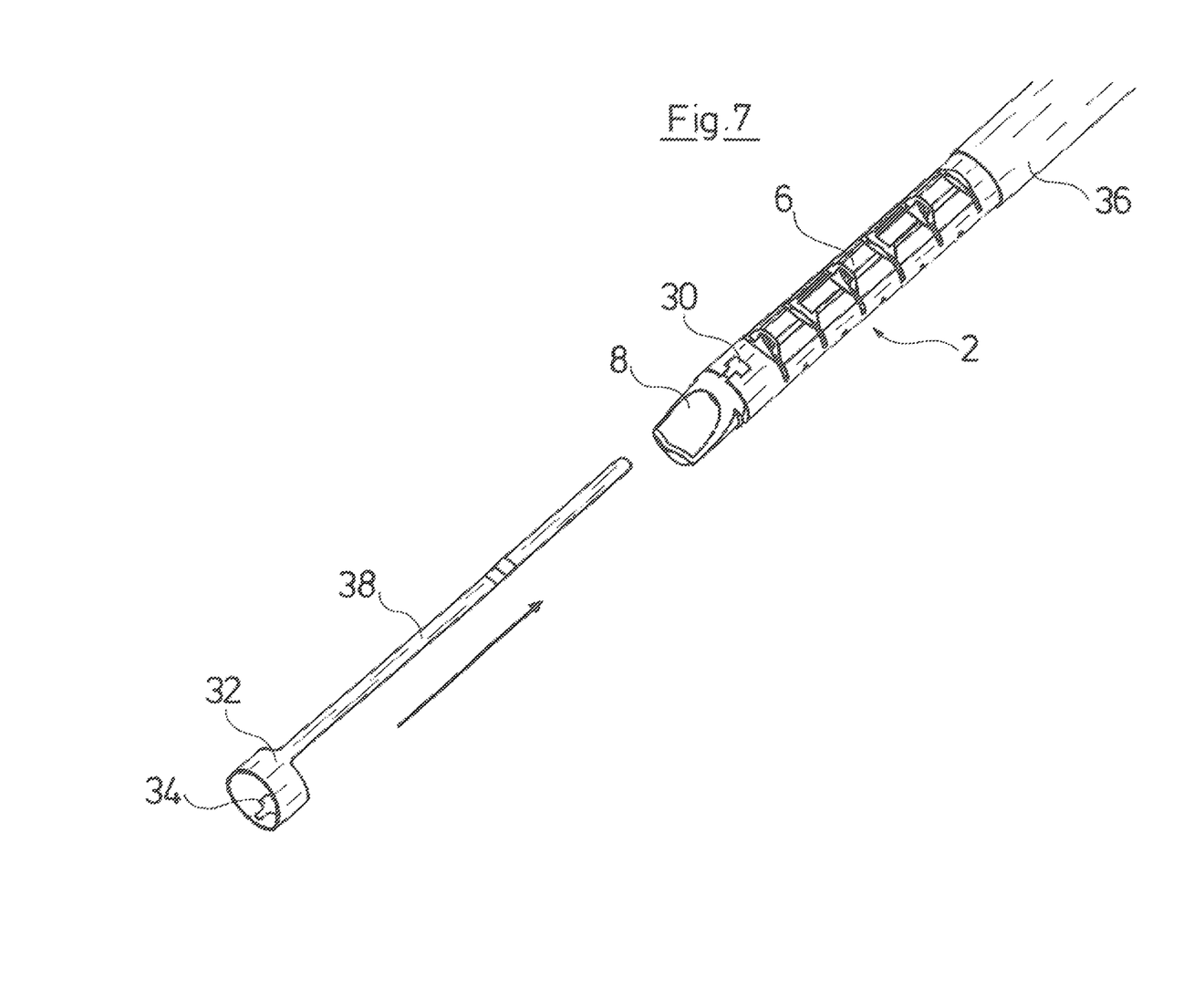
FIG. 7 is a perspective exploded representation of a distal end section of the shank, and a pull element for deflecting the bendable part of the shank.
Figure 8:
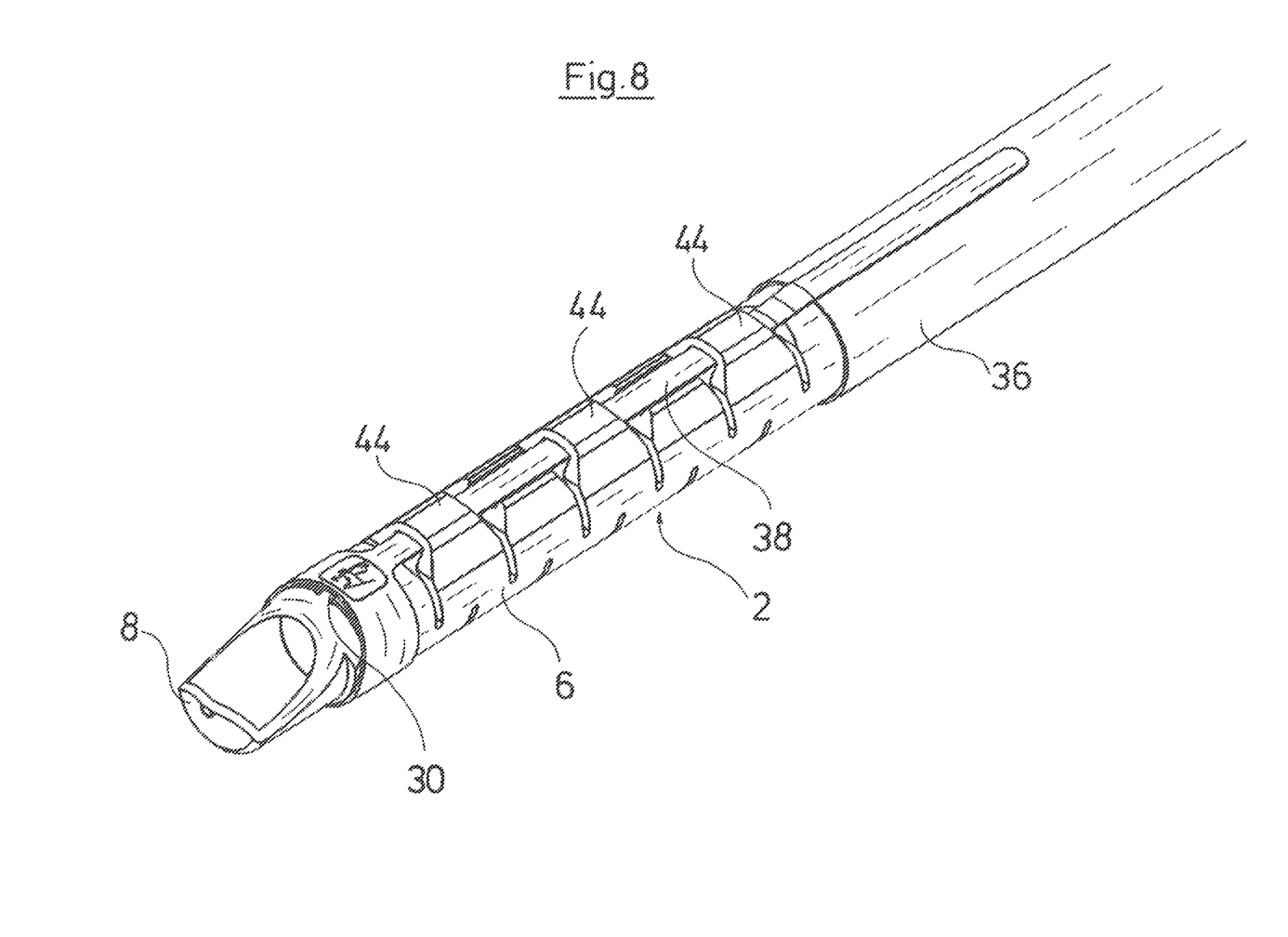
FIG. 8 is a representation according to FIG. 7, in the assembled condition.

A cylindrical sleeve 32 is provided, in order to also create a positive fixation of the part 8 of the hollow shank 2 on its part 6, in the radial direction of the hollow shank 2. This sleeve 32 has an inner cross section which corresponds to the outer cross section of the parts 6 and 8. A narrow, elongate material strip projects in the axial direction of the sleeve, at one end of the sleeve 32, and the significance of this strip will be dealt with in more detail hereinafter. The sleeve 32, with the material strip pointing in the proximal direction is applied onto the hollow shank 2 such that it covers the part 6 and the part 8, in the region of their positive connection. Hereby, the projections 30 which are formed on the part 8 of the hollow shank 2 and which not only project in the axial direction but also in the radial direction of the part 8, engage into corresponding recesses 34 of the sleeve 32 which break through the sleeve 32 is a complete manner. The sleeve 32 is fixedly connected to the part 8 of the hollow shank 2 and is therefore not movable with respect to the positive connection between the part 6 and the part 8 of the hollow shank 2, on account of this engagement of the projections 32 into the recesses 34. The sleeve 32 is additional materially connected to the part 8 of the hollow shank 2 by way of laser welding spots.

An outer tube 36 is provided for creating a positive fixation of the bendable part 6 of the hollow shank on the proximal part 4 of the hollow shank, in the radial direction of the hollow shank. This outer tube 36 which extends in the proximal direction up to the insert 10 of the handle and is fixedly connected to the insert 10 there, covers the positive connection which is formed by the projections 24 on the part 4 and the recesses 26 on the part 6, of the hollow shank 2, and thus also forms a positive fit in the radial direction of the hollow shank 2.

The hollow shank 2 is displaceable with respect to the outer tube 36 in the axial direction. For this, the hollow shank 2 is coupled in movement to a control lever 40 which is pivotably arranged on the insert 10 of the handle. The movement coupling of the hollow shank 2 to the control lever 40, but which is not represented in the drawing, is of such nature that the hollow shank 2 is moved relative to the outer tube in the distal direction when the control lever 40 is pivoted in the direction of a middle axis of the hollow shank 2.

Figure 9:
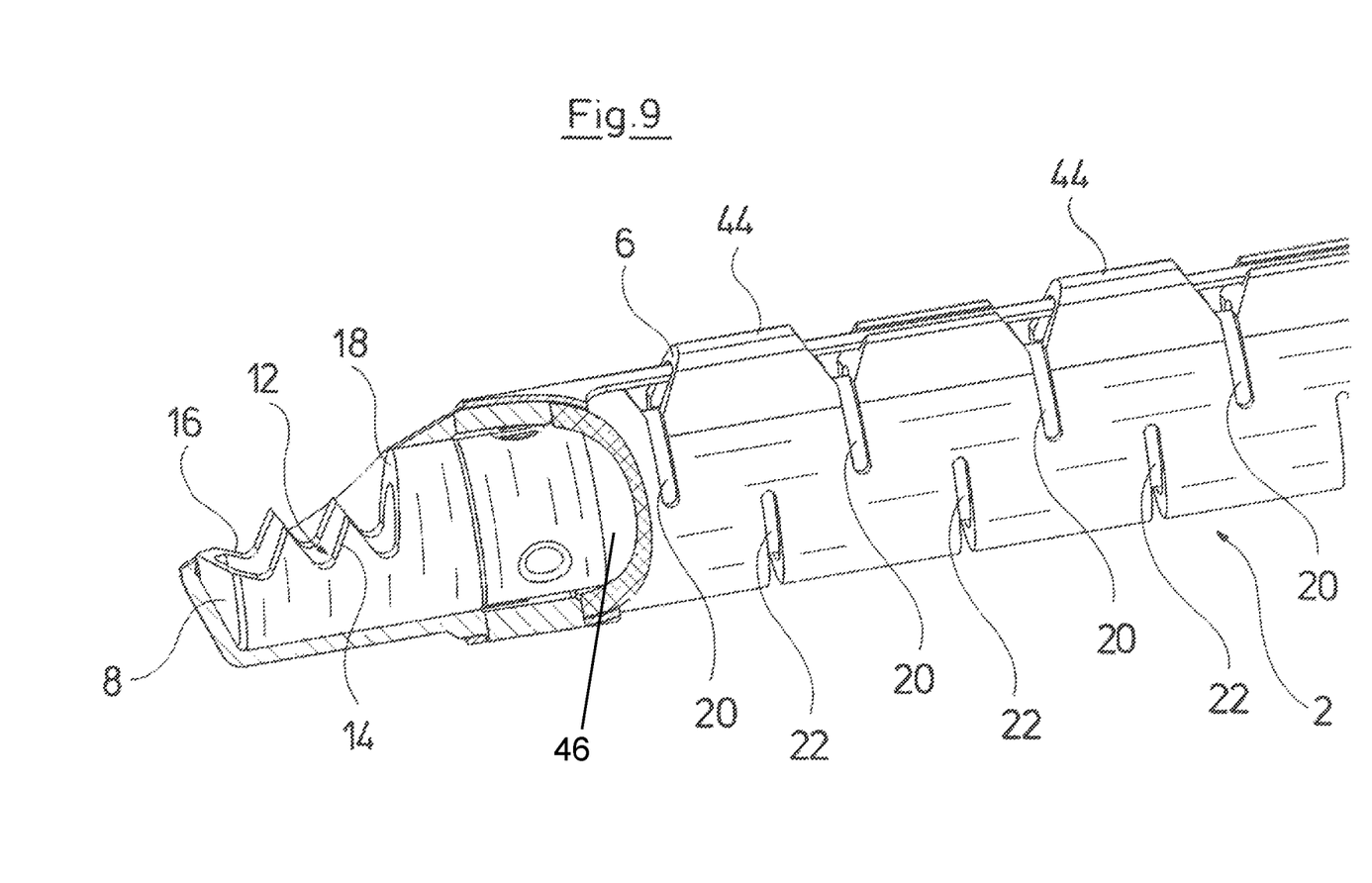
FIG. 9 is an enlarged view of the distal end section of the shank.

The metal strip which is formed on the sleeve 32 forms a pull element 38 for the control of a lateral deflection of the bendable part 6 of the hollow shank 2. The pull element 38 is designed in such a long manner that it extends beyond the distal end of the outer tube 36 and in this region is fixedly connected in this region to the outer tube 36 via a laser weld seam 42. Hereby, the pull element 36 is led in a freely movable manner through several prominences 44 which are formed radially at the outer side on the bendable part 6 of the hollow shank 2, between adjacent incisions 20, so that the pull element 38 is always located directly on the outer side of the part 6 of the hollow shank 2. A movement force acting in the distal direction is exerted onto the hollow shank 2 via the control lever 40, for the lateral deflection of the bendable part 6 of the hollow shank 2, so that the parts 4 and 6 of the hollow shank 2 move in the distal direction. However, a laterally deflection of the part 6 of the hollow shank in the direction of the pull element 38, transversely to the longitudinal extension of the hollow shank 2 is effected by way of this, since the part 8 of the hollow shank is fixedly connected to the outer tube 36 via the pull element 38 formed on the sleeve 32. As soon as the control lever 40 is let go of, the spring characteristics which are inherent of the elastically designed part 6 of the hollow shank 2 and of the pull element 38 have the effect that the hollow shank 2 is moved back in the proximal direction, and the bendable part 6 of the hollow shank again assumes a shape, in which it is aligned in the straight longitudinal extension of the proximal part 4 of the hollow shank 2.

While specific embodiments of the invention have been shown and described in detail to illustrate the application of the principles of the invention, it will be understood that the invention may be embodied otherwise without departing from such principles.

APPENDIX

List of reference numerals

2 - hollow shank
4 - part
6 - part

APPENDIX-continued

List of reference numerals

8 - part
10 - insert
12 - cutting tool
14 - cutter
16 - cutter
18 - window
20 - incision
22 - incision
24 - projection
26 - recess
28 - recess
30 - projection
32 - sleeve
34 - recess
36 - outer tube
38 - pull element
40 - control lever
42 - laser weld seam
44 - prominence
A - direction
B - direction

What is claimed is:

1. A shank instrument comprising:
an outer peripheral component;
a hollow shank comprising a proximal part, a distal part and a bendable part which is bendable transversely to a longitudinal extension of the hollow shank, between the proximal part and the distal part, and the bendable part is fixedly connected to the proximal part such that two projections formed on a peripheral wall of the proximal part connected to one another, are arranged lying opposite one another on the peripheral wall and project in a direction of a longitudinal axis of the proximal part, positively engage into two recesses to form a positive connection, the two recesses being formed lying opposite one another on the peripheral wall of the bendable part and completely pass through the peripheral wall, wherein the outer peripheral component surrounds the positive connection and at least a portion of the proximal part and at least a portion of the bendable part at an outer periphery of the proximal part and an outer periphery of the bendable part;
a sleeve, wherein the distal part is positively connected to the bendable part via another positive connection formed by the distal part and the bendable part and the sleeve is connected to the distal part and radially surrounds the another positive connection and at least a portion of the distal part and at least a portion of the bendable part of the hollow shank, wherein the sleeve connected to the distal part of the hollow shank is connected to a pull element for control of a bending of the bendable part of the hollow shank.

2. A shank instrument according to claim 1, wherein the outer peripheral component comprises an outer tube and the hollow shank is axially movable relative to the outer tube.

3. A shank instrument according to claim 1, wherein the outer peripheral component is comprised of an outer tube and the pull element is connected to the outer tube.

4. A shank instrument according to claim 1, wherein the sleeve and the pull element are formed by a common component.

5. A shank instrument according to claim 1, wherein the bendable part of the hollow shank is formed from an elastic material and comprises several incisions which run transversely to a longitudinal extension thereof, with the incisions distributed over a length thereof.

6. A shank instrument according to claim 5, wherein directly consecutive incisions are formed on wall regions of the bendable part of the hollow shank, said wall regions lying directly opposite one another.

7. A shank instrument according to claim 6, wherein:
several prominences, through which the pull element is led, are formed directly on one or more portions of the bendable part of the hollow shank, at an outer side thereof.

8. A shank instrument according to claim 1, wherein several prominences, through which the pull element is led, are formed on one or more portions of the bendable part of the hollow shank, at an outer side thereof.

9. A shank instrument according to claim 1, further comprising a drive shaft and a cutting tool, wherein the cutting tool is at least partly exposed in the distal part of the hollow shank and is driven by the drive shaft led through the hollow shank is arranged in the distal part of the hollow shank.

10. A shank instrument comprising:
an outer peripheral component;
a hollow shank comprising a rigidly configured distal part, a rigidly configured proximal part and a bendable part, the bendable part being bendable transversely to a longitudinal extension of the hollow shank, the bendable part being arranged between the rigidly configured distal part and the rigidly configured proximal part, the rigidly configured distal part comprising two projections formed on a peripheral wall of the rigidly configured distal part, the two projections being located opposite one another on the peripheral wall and the two projections projecting in a direction of a longitudinal axis of the rigidly configured distal part, the bendable part comprising two recesses, each of the recesses receiving at least a portion of one of the two projections to form a positive connection, the two recesses being located opposite one another on the peripheral wall of the bendable part and the two recesses completely passing through the peripheral wall of the bendable part, the outer peripheral component surrounding at least a portion of the hollow shank;
a sleeve connected to the distal part and radially surrounding the distal part and the bendable part of the hollow shank in the region of the positive connection formed between the distal part and the bendable part;
a pull element connected to the sleeve, the pull element being configured to control a lateral deflection of the bendable part of the hollow shank, the pull element extending from the sleeve to a position located beyond the bendable part.

11. A shank instrument according to claim 10, wherein several prominences, through which the pull element is led, are formed on one or more portions of the bendable part of the hollow shank, at an outer side thereof, wherein a portion of the bendable part is located between one of the prominences and another one of the prominences, the portion of the bendable part being free of a prominence.

12. A shank instrument according to claim 11, wherein each of the prominences covers a portion of the pull element, the portion of the bendable part not covering a portion of the pull element, wherein one end portion of the pull element is located adjacent to the sleeve and another end portion of the pull element is located adjacent to the outer component.

13. A shank instrument comprising:
an outer peripheral component;
a hollow shank comprising a rigidly configured distal part, a rigidly configured proximal part and a bendable part, the bendable part being bendable transversely to a longitudinal extension of the hollow shank, the bendable part being arranged between the rigidly configured distal part and the rigidly configured proximal part, the rigidly configured distal part comprising two projections formed on a peripheral wall of the rigidly configured distal part, the two projections being located opposite one another on the peripheral wall and the two projections projecting in a direction of a longitudinal axis of the rigidly configured distal part, the bendable part comprising two recesses, each of the recesses receiving at least a portion of one of the two projections to form a positive connection, the two recesses being located opposite one another on the peripheral wall of the bendable part and the two recesses completely passing through the peripheral wall of the bendable part, the outer peripheral component surrounding at least a portion of the hollow shank;

a sleeve connected to the distal part and radially surrounding at least the positive connection formed between the distal part and the bendable part;

a pull element connected to the sleeve, the pull element being configured to control a lateral deflection of the bendable part of the hollow shank.

14. A shank instrument according to claim 13, wherein several prominences, through which the pull element is led, are formed on one or more portions of the bendable part of the hollow shank, at an outer side thereof, wherein a portion of the bendable part is located between one of the prominences and another one of the prominences, the portion of the bendable part being free of a prominence.

15. A shank instrument according to claim 14, wherein each of the prominences covers a portion of the pull element, the portion of the bendable part not covering a portion of the pull element, the pull element extending from the sleeve to a position located beyond the bendable part.

16. A shank instrument according to claim 13, wherein the pull element extends about only a portion of a circumference of the hollow shank, wherein a portion of the pull element is in contact with the outer peripheral component.

* * * * *